United States Patent [19]
Pritchard

[11] Patent Number: 5,615,687
[45] Date of Patent: Apr. 1, 1997

[54] HEART MONITORING SYSTEM AND METHOD WITH REDUCED SIGNAL ACQUISITION RANGE

[75] Inventor: Bruce A. Pritchard, McMinnville, Oreg.

[73] Assignee: Hewlett-Packard Company, Palo Alto, Calif.

[21] Appl. No.: 567,975

[22] Filed: Dec. 6, 1995

[51] Int. Cl.⁶ .................................................. A61B 5/0402
[52] U.S. Cl. .................................................................. 128/696
[58] Field of Search .................................. 128/901, 902, 128/696; 607/62

[56] References Cited

U.S. PATENT DOCUMENTS

| | | | |
|---|---|---|---|
| 4,530,365 | 7/1985 | Harada et al. | 128/902 |
| 4,890,630 | 1/1990 | Kroll et al. | 128/696 |

FOREIGN PATENT DOCUMENTS

| | | | |
|---|---|---|---|
| 5003861 | 1/1993 | Japan | 128/696 |
| 5220121 | 8/1993 | Japan | 128/696 |

*Primary Examiner*—William E. Kamm
*Assistant Examiner*—George R. Evanisko

[57] ABSTRACT

An ECG system for a 12-lead ECG test includes ten electrodes—consisting of six ventricle electrodes V1–V6, a right arm electrode RA, a left arm electrode LA, a left leg electrode LL, and a right leg electrode RL—which generate electrical signals indicative of heart activity within a human patient. The EGG system also includes a plurality of conductors connected to corresponding electrodes and a signal acquisition system connected to the conductors. The EGG system also has an offset adjustment system operatively coupled to the signal acquisition system. The offset adjustment system identifies a selected voltage level (such as a maximum or minimum voltage level) of at least one of the electrical signals generated by an associated electrode and manipulates that voltage level to produce an offset adjustment signal. This offset adjustment signal is used to bring voltage levels of all of the electrical signals produced by the electrodes within a signal acquisition range of the signal acquisition system. The ECG system further includes a potential adjusting feedback circuit coupled between the offset adjustment system and one of the electrodes (such as the right leg electrode RL) to supply a reference potential to that electrode. The potential tends toward the offset adjustment signal to offset the electric potentials of the human patient by an equal amount. This offset has the effect of moving the range of electrode voltages into the range of the signal acquisition system and yields a maximum signal acquisition range of approximately 300 mV, which can be resolved to 5 µV increments using a 16-bit A/D converter.

17 Claims, 3 Drawing Sheets

HEART MONITORING SYSTEM AND METHOD WITH REDUCED SIGNAL ACQUISITION RANGE

TECHNICAL FIELD

This invention relates to heart monitoring systems, such as electrocardiograph systems, and methods for measuring heart activity in a human patient.

BACKGROUND OF THE INVENTION

An electrocardiograph (ECG) system monitors heart activity in a human patient. The ECG system applies small conductive pads or "electrodes" to specific locations on the human patient. Each electrode has an adhesive patch and a conductive member (which might be one in the same) that is placed on the patient's skin. These electrodes detect electrical impulses generated by the heart during each beat. Each heart beat generates a waveform that consists of three identifiable wave complexes referred to as the P, QRS, and T wave complexes.

To appropriately capture the heart beat waveform, a conventional 12-lead resting ECG is conducted using ten electrodes. An electrode is adhered to each of the four limbs of the human patient—left arm, right arm, left leg, and right leg—and to six anatomically-prescribed locations across the chest and left side of the human patient.

In response to detection of the electrical impulses from the heart, the electrodes produce electrical signals indicative of the heart activity. These electrical signals have small magnitudes on the order of 1 mV, and are commonly resolved by signal processes down to about 5 μV. The electrical signals are different from one another by virtue of the different physical locations of the electrodes about the patient. FIG. 1 shows a diagrammatic representation of a conventional ECG system 10 having ten electrodes V1–V6, RA, LA, LL, and RL connected to a human patient 12. The electrodes are connected to an ECG device 14 via conductors 16. ECG device 14 detects the electrical signals generated by the electrodes and performs various signal processing and computational operations to convert the raw electrical signals into meaningful information that can be displayed or printed out for review by a physician.

From the signals produced by the ten electrodes, ECG device 14 can produce two sets of ECG leads: limb leads and chest leads. The "limb leads" are formed from the right arm electrode RA, the left arm electrode LA, and the left leg electrode LL as follows:

I=LA–RA

II=LL–RA

III=LL–LA aVR=RA–½(LA+LL)

aVL=LA–½(RA+LL)

aVF=LL–½(LA+RA)

In addition to these six leads, six "chest leads" are formed by subtracting the average of the right arm, left arm, and left leg electrode outputs from each of the chest electrodes V1–V6, as follows:

Lead V1=V1–(RA+LA+LL)/3

Lead V2=V2–(RA+LA+LL)/3

Lead V3=V3–(RA+LA+LL)/3

Lead V4=V4–(RA+LA+LL)/3

Lead V5=V5–(RA+LA+LL)/3

Lead V6=V6–(RA+LA+LL)/3.

Notice that each of these twelve ECG leads of a conventional 12-lead ECG test concerns input from only three of the four limb electrodes: the right arm electrode RA, the left arm electrode LA, and the left leg electrode LL. According to medical convention, the right leg electrode RL is not used in deriving a multi-channel ECG recording. Part of this is due to the RL electrode being located farthest from the heart in comparison to the other nine electrodes.

The right leg electrode RL is used, however, to help reduce common-mode interference that appears between the signal leads and a common reference plane. As illustrated in FIG. 1, it is common for the patient to have an electric potential $V_{P-E}$ relative to a true electrical earth ground, while the ECG device has a relative or floating ground ECG GND that is at a different electric potential $V_{E-ECG}$ relative to true earth ground. Typically, ECG device 14 is configured so that its own ground ECG GND tries to approximate true earth ground, thereby leaving a difference in potential between the patient 12 and ECG device 14. These different potentials cause common-mode noise voltage in the electrode signals carried by conductors 16 which appears equally and in phase from each electrode/conductor relative to ground.

Conventional ECG systems are designed to reject the common-mode signals. Because each electrode leadwire has the same common mode signal, the 12 lead tests described above are each derived by subtracting different ones of the electrical signals so that theoretically the common mode interference is removed. However, subtraction alone may not completely eliminate the common mode interference because there is such a significant difference in magnitudes between the common mode signal and the small signals being detected by the electrodes. For example, an electric potential of a human patient relative to electric earth ground might be 5–10 volts, which is one to several orders of magnitude greater that the 1 mV signal detected by the electrode and the resolvable unit of 5 μV. Simply subtracting signals at the 5–10 volt range might result in missing important information at the 1 mV or less range.

Accordingly, it is conventional to apply a small correcting current to the right leg electrode RL in an effort to bring the electric potential of the human patient and the relative ground of the ECG system in line with each other. As diagrammatically shown in FIG. 1, the RL electrode is driven in such a way that the patient-to-earth ground voltage potential $V_{P-E}$ and the ECG device-to-earth ground potential $V_{E-ECG}$ are approximately equal, thereby substantially removing the common mode interference before the EGG even conducts the lead computations. Conventionally, the RL electrode is based upon the average of the other three limb electrodes RA, LL, and LA. An operational amplifier 22 provides a correcting current based upon a difference between the average voltage from these three limbs and the EGG GND.

Designers of EGG systems are also cognizant of the need to accommodate DC offset voltages which may exist between leadwires, originating from electrochemical mechanisms inherent to the skin-electrode interfaces. Performance standards (e.g., ANSI) require an accuracy in signal detection over a 300 mV range. To test compliance with these standards, a designer conducts a test where one conductor is driven to +300 mV relative to all other conductors and a reading is taken to detect electrical signals. Then that same conductor is driven to −300 mV relative to all other conductors and another reading is taken. This action is repeated for each of the conductors. The system passes if signals can be detected over the entire ±300 mV range.

As shown in FIG. 1, ECG device 14 typically has an amplifying subsystem 18 which amplifies the analog signals generated by the electrodes and an analog-to-digital (A/D) converter 20 which converts the amplified analog signals into digital values that are resolved down to approximately 5 µV. To accommodate a 600 mV (i.e., ±300 mV) signal acquisition range, a 17-bit A/D converter is used to account for the 120,000 resolvable increments (i.e., 600 mV/5 µV). Other techniques might alternatively be used to detect signals within the 600 mV range, such as a hardware high-pass pole.

It would be beneficial to reduce the dynamic range from 600 mV to a narrower signal acquisition range. This reduction would simplify the signal acquisition circuitry, and lower its cost, while still complying with medical requirements. For instance, a reduction by one-half to a 300 mV acquisition range would permit a designer to employ conventional, off-the-shelf $2^n$ devices (e.g., 16-bit A/D converter) to capture the signals, rather than unconventional electronics like the illustrated 17-bit A/D converter that is used to detect signals within the 600 mV range.

It is an aspect of this invention to provide an ECG system that satisfies the requirements for offset range and resolution, as specified by ANSI and others, while operating within a reduced dynamic range for signal detection.

SUMMARY OF THE INVENTION

This invention provides a heart monitoring system that continuously and dynamically drives the ECG GND to a value based upon a selected voltage level (such as the minimum or maximum voltage level) output from one or more of the electrodes, as opposed to a fixed combination of electrode signals. By using a voltage level based on an electrode output as a reference potential, rather than ECG GND, the dynamic signal acquisition range is reduced by one-half to approximately 300 mV from the traditional 600 mV plus range. As a result, less complex and less expensive acquisition circuitry, such as a 16-bit A/D converter, can be used for the signal conversion process.

According to one aspect of this invention, an ECG system includes a plurality of electrodes adapted to be connected to a human patient. In a conventional 12-lead ECG test, these electrodes consist of the six electrodes V1–V6, the right arm electrode RA, the left arm electrode LA, the left leg electrode LL, and the right leg electrode RL. The electrodes generate electrical signals indicative of heart activity within the patient. The ECG system also includes a plurality of conductors connected to corresponding electrodes and a signal acquisition system connected to the conductors. The signal acquisition system has a signal acquisition range and detects the electrical signals with voltage levels that fall within the signal acquisition range.

The ECG system also has an offset adjustment system operatively coupled to the signal acquisition system. The offset adjustment system identifies a selected voltage level (such as a maximum or minimum voltage level) of at least one of the electrical signals generated by an associated electrode and manipulates that voltage level to produce an offset adjustment signal. This offset adjustment signal is used to bring voltage levels of all of the electrical signals produced by the electrodes within the signal acquisition range of the signal acquisition system. The ECG system further includes a potential adjusting feedback circuit coupled between the offset adjustment system and one of the electrodes (such as the right leg electrode RL) to supply a potential to that electrode. The potential moves toward the offset adjustment signal to offset the electric potentials of the human patient by an equal amount. This offset has the effect of moving the range of electrode voltages into the range of the signal acquisition system and yields a maximum signal acquisition range of approximately 300 mV.

According to another aspect of this invention, a method for monitoring heart activity in a human patient is described. According to the method, multiple electrical signals indicative of heart activity within the patient are generated. These electrical signals have associated voltage levels. The signals that fall within a signal acquisition range are then acquired. From these signals, a selected voltage level of at least one of the electrical signals is identified and manipulated to produce an offset adjustment signal. A reference potential is then derived to approximate the offset adjustment signal. The reference potential is applied to the patient to thereby drive the range of electric potentials of the human patient into the range of the signal acquisition system.

DETAILED DESCRIPTION OF THE PREFERRED EMBODIMENT

For purposes of the following discussion, all voltages are described as referenced to ECG GND. The common mode voltage of the ECG GND (relative to earth ground) is driven to track the common mode voltage of the patient (relative to earth ground) as described in the Background of the Invention section. From the viewpoint of the ECG GND, the net effect is that the common mode voltage of the patient can be controlled.

Figure 2:
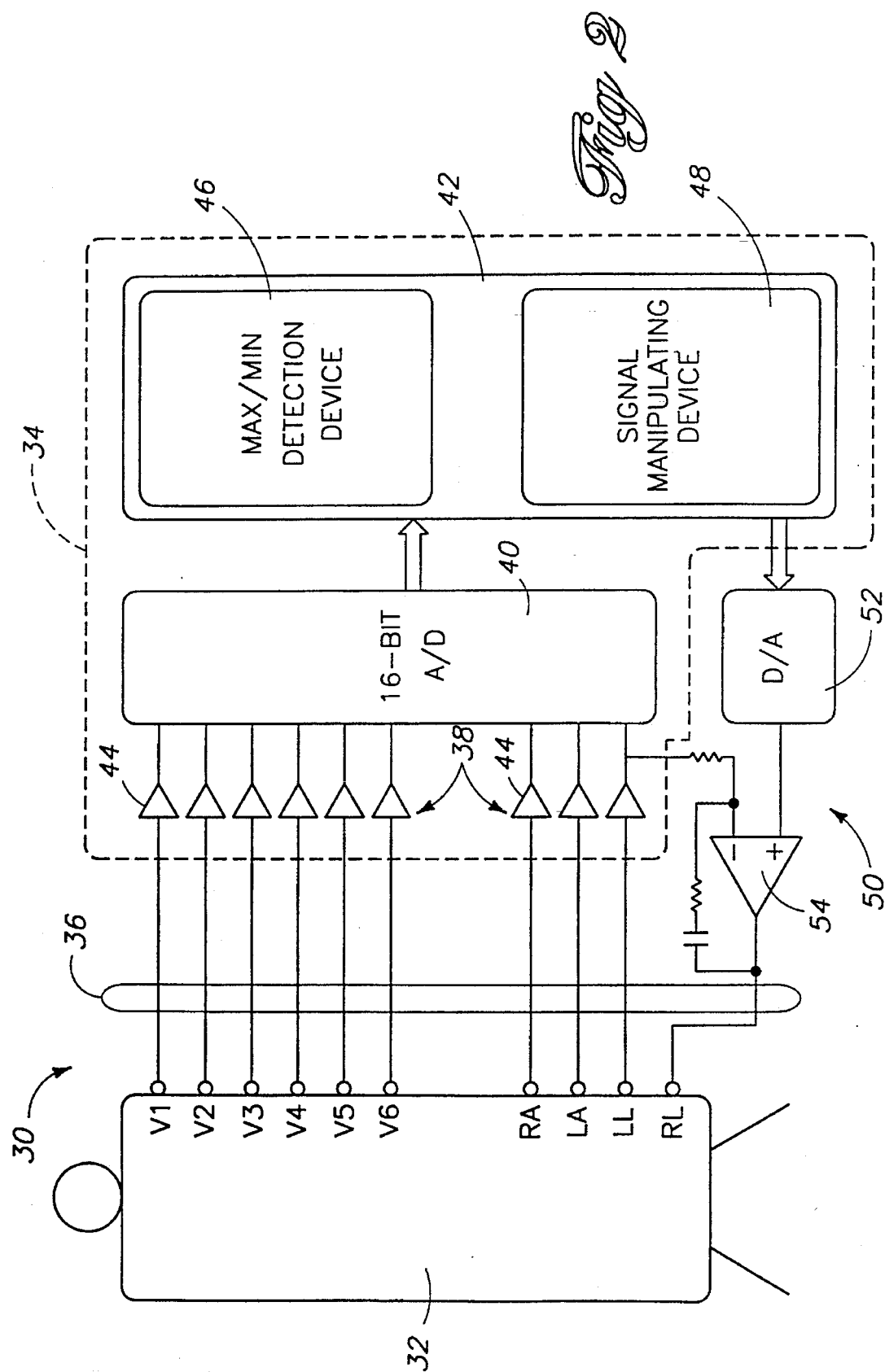
FIG. 2 is a diagrammatic illustration of an ECG system according to an implementation of this invention.

FIG. 2 shows a heart monitoring system implemented as an ECG system 30 according to one aspect of this invention. ECG system 30 includes ten electrodes for conducting a 12-lead ECG test on a human patient 32. The electrodes are positioned at well known anatomically-selected locations on human patient 32. These electrodes consist of six ventricular electrodes V1–V6, a right arm electrode RA, a left arm electrode LA, a left leg electrode LL, and a right leg electrode RL as is common in a 12-lead EGG test. The electrodes measure heart activity within patient 22 and generate electrical signals indicative of such heart activity.

The electrodes are connected to an EGG device 34 via conductors 36. ECG device 34 detects and processes the signals generated by the electrodes. ECG device 34 calculates numerical results which are informative to a physician or other health care provider. One suitable ECG device 34 is the commercially available PageWriter XLi cardiograph produced by Hewlett-Packard Company, modified to include a signal acquisition system, an offset adjustment system, and feedback circuitry, which is described below in more detail with reference to FIG. 2. This cardiograph computes more than 800 numerical results, collectively known as the "measurement matrix", which are stored in a measurement table. The waveforms captured by the electrodes and these numerical computations are provided to the health care provider via a monitor display or an EGG printout. The techniques for detecting and processing ECG waveforms are known and thus are not described in detail herein.

For purposes of continuing explanation, EGG device 34 is shown as comprising a signal acquisition system having an amplifying subsystem 38 and an A/D converter 40. The ECG device 34 is also shown as having an offset adjustment system 42. The other conventional components of ECG device 34 are not shown to simplify discussion of the present invention. In the illustrated implementation, amplifying subsystem 38 comprises individual amplifiers 44 resident at ECG device 34 to amplify the electrical signals generated by the electrodes. In other implementations, however, amplifying subsystem 38 can be located remote from the ECG device 34 in its own housing near the patient, or at the individual electrodes themselves.

Amplifying subsystem 38 has a set of inputs electrically coupled to nine of the electrodes via associated conductors 36. The amplifying subsystem 38 also has a set of corresponding outputs to output amplified signals to A/D converter 40. According to this configuration, the electrical analog signals produced by electrodes V1–V6, RA, LA, and I,L are carried via conductors 36 to amplifying subsystem 38, where they are amplified. The amplified signals are then passed to A/D converter 40 which converts the analog signals to digital values that can be processed and used for computational derivations.

The electrical signals generated by the electrodes and then amplified have associated voltage levels. The signal acquisition system has a signal acquisition range that is less than conventional systems, and is preferably only approximately 300 mV. The signal acquisition system is capable of detecting and converting electrical signals with voltage levels that fall within the 300 mV signal acquisition range. As described more fully below, the A/D converter 40 of the signal acquisition system is preferably a conventional 16-bit A/D converter.

Offset adjustment system 42 is operatively coupled to A/D converter 40 via a multi-bit bus. The offset adjustment system identifies a selected voltage level of at least one of the electrical signals and manipulates that voltage level to produce an offset adjustment signal. This offset adjustment signal is used to bring voltage levels of all of the electrical signals produced by the electrodes within the signal acquisition range of the signal acquisition system.

In the illustrated embodiment, the offset adjustment system 42 includes a maximum/minimum voltage level detection device 46 which identifies the maximum or minimum voltage level of the nine electrical signals output from the electrodes V1–V6, RA, LA, and LL. More specifically, max/min detection device 46 detects the maximum or minimum digital value that is output from A/D converter 40. The maximum or minimum values are detected to help generate a reference ceiling or floor voltage to which all other signals are relative. This is useful for narrowing the dynamic signal acquisition range to approximately 300 mV, as will become more clear from the continuing discussion. Preferably, max/min detection device 46 is configured to detect either the maximum voltage level or the minimum voltage level. The max/min detection device is shown, however, as a maximum/minimum detector to demonstrate that it can be optimized to detect either extreme. Furthermore, it is noted that the device can be configured to detect some other selected voltage level, such as the mid-point between the maximum and minimum extremes.

The offset adjustment system 42 further includes a signal manipulating device 48 which computes the offset adjustment signal as a function of the maximum or minimum voltage level detected by the max/min detection device 46.

Preferably, the signal manipulating device 48 receives a combination of (1) the maximum or minimum voltage level from the max/min detection device 46 and (2) a voltage level of another one of the electrical signals from the electrodes. From these two inputs, the signal manipulating device 48 produces an offset adjustment signal as a function of both. As an example of one implementation, the signal manipulating device 48 computes an offset adjustment signal equal to a difference between the maximum or minimum voltage level and at least one other voltage level, such as the voltage level produced by the left leg LL electrode, plus a desired offset voltage to center the leadwire voltages within a signal acquisition range.

In the illustrated embodiment, the offset adjustment system 42 is implemented as a processor, such as microprocessor or a specially designed ASIC. The max/min detection device 46 and the signal manipulating device 48 are firmware-based components programmed into the processor to perform the above described functions. However, the offset adjustment system 42, max/min detection device 46, and the signal manipulating device 48 can alternatively be implemented in discrete hardware components.

ECG system 30 also includes a potential adjusting feedback circuit 50 which effectively adjusts the electric potential on human patient 32 toward a desired reference potential. Potential adjusting feedback circuit 50 is electrically coupled between the offset adjustment system 42 and one of the electrodes to supply a correcting current to the patient. In FIG. 2, feedback circuit 50 is coupled to the right leg electrode RL, although other coupling configurations can be employed. The correcting current is derived from a difference between the offset adjustment signal and one or more electrode voltages (such as the voltage level for electrode LL) to drive the range of electric potentials of the human patient to within a predetermined acquisition range of the amplifier and A/D converter. The potential adjusting feedback circuit 50 is preferably resident at ECG device 34.

In the preferred implementation, potential adjusting feedback circuit 50 has a digital-to-analog (D/A) converter 52 to convert the offset adjustment signal from the offset adjustment system 42 back into an electrical analog signal. Feedback circuit 50 further includes an inverting integrating operational amplifier (op amp) 54 coupled between the D/A converter and the right leg electrode RL.

As illustrated in FIG. 2, op amp 54 has a first or negative input coupled to the amplified output that corresponds to the left leg electrode LL, a second or positive input coupled to D/A converter 52, and an output coupled to the right leg electrode RL. In other implementations, more than one amplified output can be collectively input to the negative terminal of op amp 54. For instance, a resistance path can be provided between all three appendage electrodes RA, LA, and LL so that the negative input of op amp 54 receives a voltage equal to the average of the voltages from electrodes RA, LA, and LL. However, tier simplification purposes, the illustrated embodiment only shows a single amplified output coupled to the negative terminal of op amp 54.

Feedback op amp 54 derives an electrical analog signal based upon a differential between the amplified signal from electrode LL and the analog signal from D/A converter 52. The feedback loop causes the voltage on the left leg electrode LL to approximate the voltage delivered to the positive terminal of op amp 54 from D/A 52. Said another way, the negative feedback implementation drives the voltages at the positive and negative inputs to the op amp 54 to be approximately equal. This occurs because as the voltage from electrode LL goes higher than the voltage signal output by the D/A 52, the op amp 54 will output a negative differential voltage to the right leg electrode. The differential signal output by op amp 54 offsets the electric potentials of human patient 32 by the same amount, thereby lowering the voltage of left leg electrode LL back toward the D/A output voltage from D/A 52. Generation of a proper offset adjustment signal from the signal manipulating device 48, which is converted to the analog voltage applied at the positive terminal of the op amp 54, can thereby control the electric potentials of all leadwires to converge within a narrower acquisition range of the signal measurement system.

One example technique for initializing the ECG system 30 and producing a suitable offset adjustment signal will now be described. Suppose the signal acquisition range is 0 to 327.68 mV (where the upper limit of 327.68 mV is equal to the 5 µV increments times $2^{16}$). Initially, the offset adjustment signal is set to a value that converts to an arbitrary voltage at the positive input terminal at op amp 54. For example, suppose this arbitrary voltage is 164 mV which is approximately the mid-point in the signal acquisition range. Due to the negative feedback configuration of circuit 50, the voltage at the left leg electrode LL will approximate the voltage applied to the positive terminal, and thus, will also be at 164 mV.

The offset adjustment system 42 observes the values from the nine electrodes. According to conventional techniques for hooking up the electrodes under known standards such as ANSI, the electrodes will be at potentials within a 300 mV range of each other. If one or more electrode voltages initially fills outside of the 0 to 327.68 mV measurement range afforded by the 16-bit A/D 40, as indicated by a voltage pegged at the minimum limit of 0 volt or maximum limit of 327.68 mV, the signal manipulating device 48 iteratively modifies the offset adjustment signal to change the potential applied to the RL electrode, thereby changing the potentials on the other electrodes. The values are then examined again to see if they fall within the signal acquisition range. The examine-and-iteratively-change process is repeated until all signals fall within the 0 to 327.68 range.

Following this initialization, the signal manipulating device 48 computes a value which converts to an analog voltage $V_+$ that will maintain the following relationship:

$$V_+ = V_- - V_{min} + V_{offset}$$

where $V_-$ is the voltage at the negative input terminal of op amp 54, $V_{min}$ is the minimum voltage from the nine electrodes, and $V_{offset}$ is a selected offset voltage to center the range of electrode voltages within the 0 to 327.68 mV range. For example, $V_{offset}$ can be set to a constant 14 mV (which assumes $V_{max} - V_{min}$ is approximately 300 mV), or computed more precisely as:

i $V_{offset} = [327.68 \text{ mV} - (V_{max} - V_{min})]/2$.

Since the feedback loop is continually driving the positive and negative terminals toward the same voltage (i.e., $V_+ = V_-$), the above equation produces $V_{min} = V_{offset} = 14$ mV for the case where $V_{max} - V_{min} = 300$ mV. This means that $V_{max}$ equals 314 mV. The leadwires can thereby vary somewhat, yet still be captured within the signal acquisition range. For instance, the leadwire with the minimum voltage can go 14 mV more negatively and the leadwire with the maximum voltage can go 13.68 mV more positively. If the maximum voltage starts to wander even higher or the minimum voltage starts to wander even lower, the signal manipulating device 48 produces a value to maintain the relationship defined above. This continual correction keeps the voltages from the electrodes within the 327.68 mV range.

To provide a further example, suppose that the maximum voltage of any of the leadwires is on electrode V6, and that its voltage is +300 mV relative to the voltage on left leg electrode LL that is input to the op amp 54. The voltages on all other electrodes fall between these two voltages. The D/A converter 52 can be controlled by the offset adjustment system 42 to deliver 14 mV to the positive terminal of the op amp 54. Due to the negative feedback configuration of circuit 50, the voltage on electrode LL at the negative terminal of the op amp 54 is driven toward 14 mV. This essentially causes an equal 14 mV offset to all of the electrodes so that the electrode voltages now fall between 14 mV (for electrode LL) and 314 mV (for maximum electrode V6). As a result, all signals fall within the signal acquisition range of 0 to 327.68 mV. Now suppose that the electrode V6 has the minimum voltage of −300 mV relative to the voltage on left leg electrode LL. In this situation, the D/A converter 52 can be controlled to deliver +314 mV to op amp 54, thereby effectively raising the voltage of electrode LL to +314 mV. This essentially causes an equal 314 mV offset to all of the electrodes so that they now fall between 14 mV (for minimum electrode V6) and 314 mV (for electrode LL). Again, these voltages fall within the signal acquisition range of A/D converter 40 of 0 to 327.68 mV.

Figure 1:
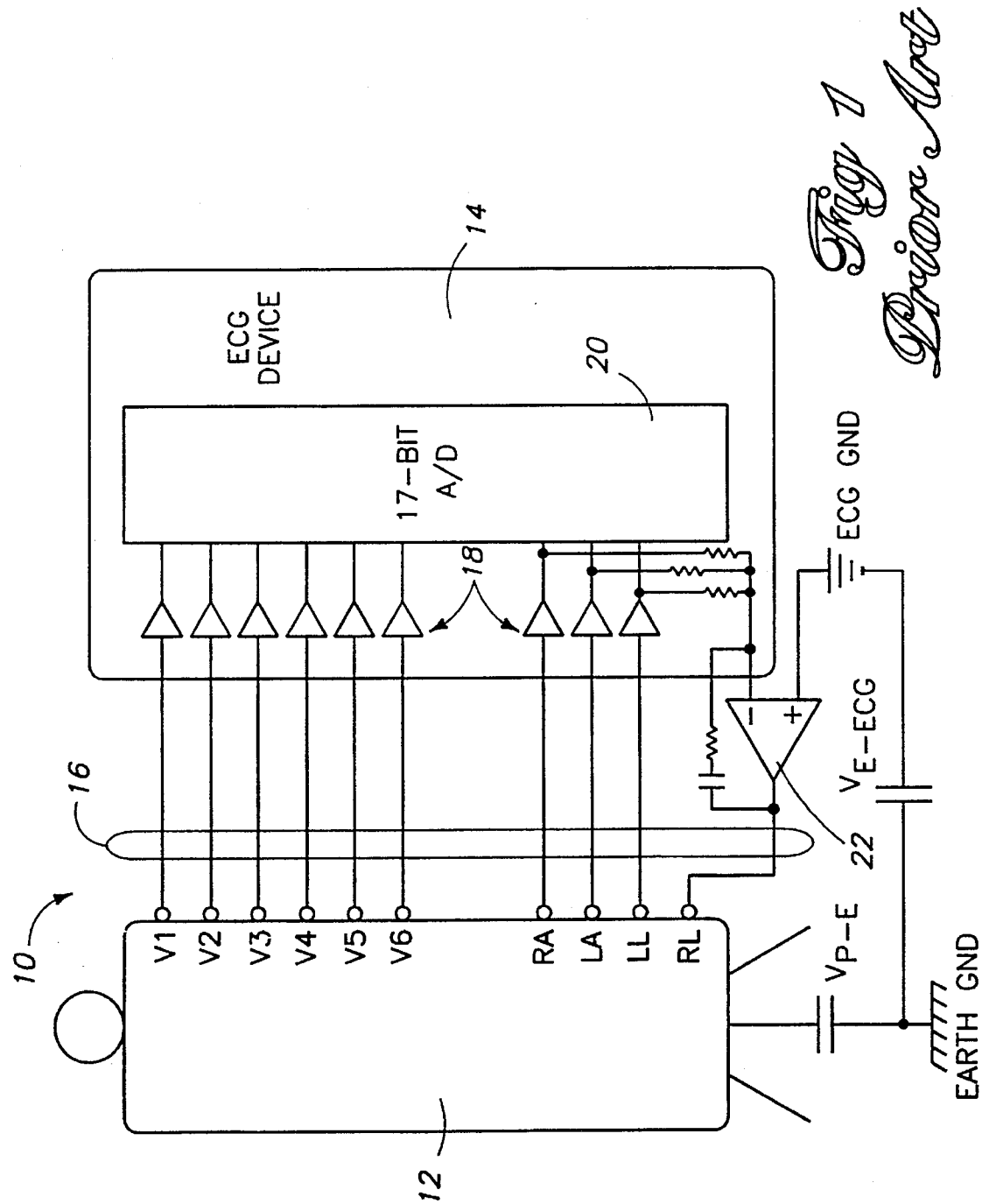
FIG. 1 is a diagrammatic illustration of a prior art ECG system.

Thus, the maximum range for the signal acquisition system is only 327.68 mV, not the conventional range of greater than 600 mV as is required by a fixed reference voltage at the positive terminal of the op amp 22 in the prior art FIG. 1 embodiment. As a result, a standard 16-bit A/D converter (which provides $2^{16}$=65,536 steps) can be used to resolve the 300 mV range into 5 µV increments.

In some circumstances, one electrode can become grossly out of line with the acquisition range. One example case is a leadwire off condition in which the electrode has become detached from the patient, causing a significant voltage change for that electrode. In such events, the system can go into a diagnostics mode to determine which electrode is the source of the extreme voltage diferential and alert the operator. These diagnostics are conventional.

Figure 3:
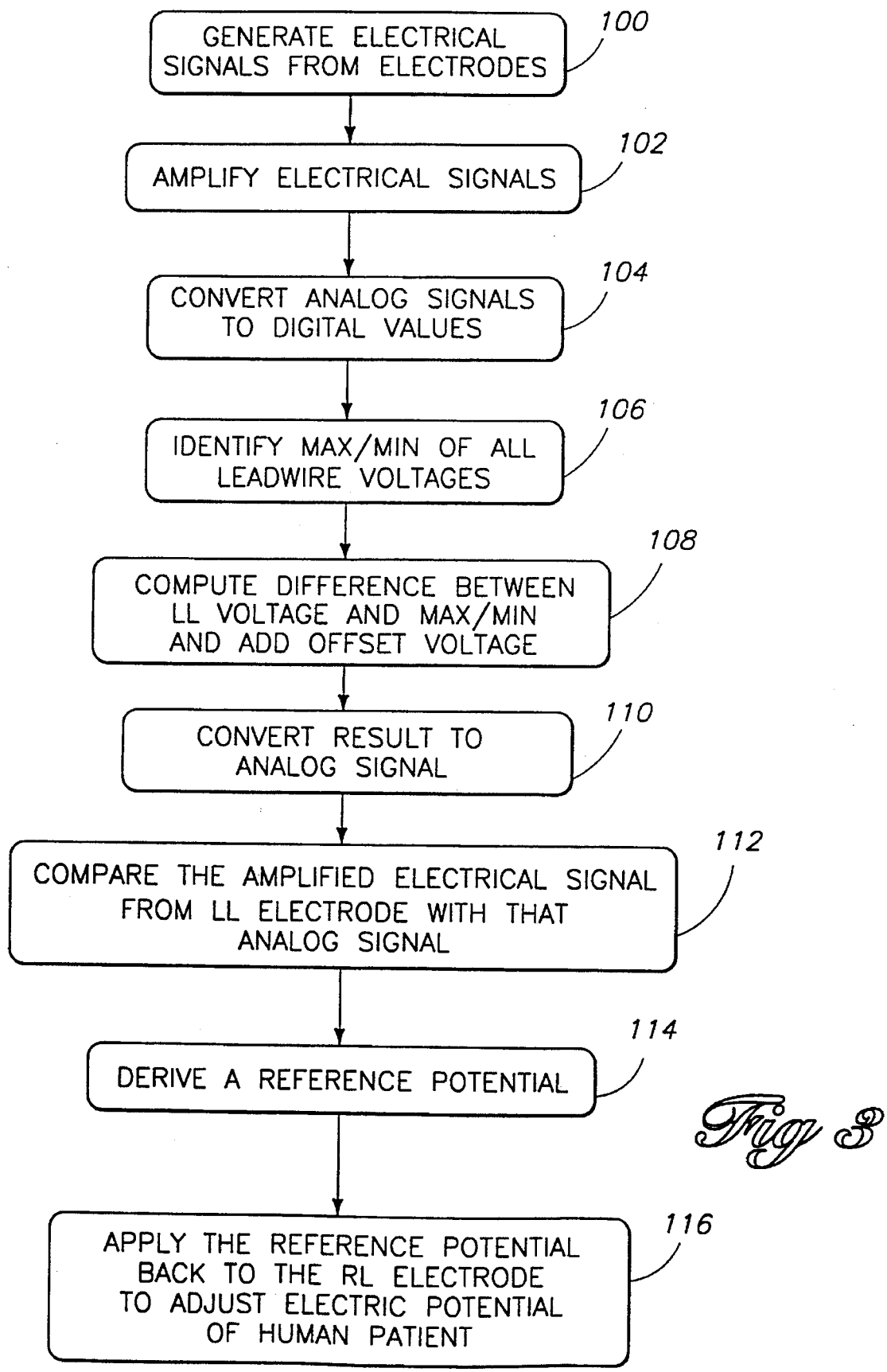
FIG. 3 is a flow diagram of a method for monitoring heart activity in a human patient.

FIG. 3 shows a method for monitoring a patient's heart activity according to another aspect of this invention. At step 100, the electrodes generate electrical signals indicative of heart activity in the human patient. The electrical signals are amplified by amplifying subsystem 38 (step 102) and output to 16-bit A/D converter 40. At step 104 the analog signals are converted to digital values indicative of the voltage levels. Max/min detection device 46 of offset adjustment system 42 then identifies either a maximum or minimum value from among the multiple electrical signals (step 106). At step 108, the signal manipulating device 48 computes an offset adjustment signal equal to the difference between the voltage at left leg electrode LL and the maximum or minimum value, plus an offset voltage $V_{offset}$. At step 110, the offset adjustment signal is converted by D/A converter 52 back into an analog signal. This analog signal is then compared by op amp 54 to an amplified signal from the left leg electrode LL (step 112). Op amp 54 produces a reference potential from this comparison which is effective to urge the LL electrode voltage toward the offset adjustment signal output from the op amp 54 (step 114). The reference potential is applied to the right leg electrode RL to adjust the electrical potential of human patient 32 such that the voltage of electrodes V1–V6, RA, LA, and LL remain within the signal acquisition range (step 116).

The ECG system of this invention is advantageous in that it reduces the A/D range to approximately 300 mV, or approximately one-half of the customary 600 mV range. This reduced range complies with the electrode offset requirements as described by ANSI and others, while requiring less expensive and less complex A/D circuitry. For instance, a standard 16-bit A/D converter can be used, rather than an expensive 17-bit A/D converter.

The invention has been described in the context of an ECG system. However, aspects of this invention can be used in other applications including ECG monitoring equipment, telemetry, Holter, and other ECG-sensing. Aspects might also be employed in non-ECG equipment such as an EEG system.

In compliance with the statute, the invention has been described in language more or less specific as to structural and methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method for monitoring heart activity in a human patient, the method comprising the following steps:
   receiving a plurality of electrical signals indicative of heart activity of the patient, the electrical signals having associated variable voltage levels;
   acquiring the electrical signals having voltage levels that fall within a predetermined signal acquisition range;
   computing a difference between a voltage level of at least one of the acquired electrical signals and a voltage level of at least one other of the electrical signals to produce an offset adjustment signal;
   extracting a reference signal from at least one of the electrical signals; and
   deriving a potential for application to the patient from the offset adjustment signal and a reference signal to maintain the voltage levels of the received electrical signals within the signal acquisition range.

2. A method as recited in claim 1, further comprising the step of applying the potential to the patient to maintain the voltage levels of the received electrical signals within the signal acquisition range.

3. A method for monitoring heart activity in a human patient, the method comprising the following steps:
   receiving a plurality of electrical signals indicative of heart activity of the patient, the electrical signals having associated variable voltage levels;
   acquiring the electrical signals having voltage levels that fall within a predetermined signal acquisition range;
   determining a voltage level from among the plurality of electrical signals;
   producing an offset adjustment signal using the determined voltage level;
   extracting a reference signal from at least one of the electrical signals; and
   deriving a potential for application to the patient from the offset adjustment signal and a reference signal to maintain the voltage levels of the received electrical signals within the signal acquisition range.

4. A method as recited in claim 3, wherein:
   the producing step comprises computing a difference between the determined voltage level and a voltage level of at least one other of the electrical signals for use in determining the offset adjustment signal.

5. A method as recited in claim 3, further comprising the step of applying the potential to the patient to maintain the voltage levels of the received electrical signals within the signal acquisition range.

6. A method for monitoring heart activity in a human patient, the method comprising the following steps:
   receiving a plurality of electrical signals indicative of heart activity of the patient, the electrical signals having associated variable voltage levels;
   acquiring the electrical signals having voltage levels that fall within a predetermined signal acquisition range;
   producing an offset adjustment signal using at least one of the acquired electrical signals; and
   producing a difference between the offset adjustment signal and a voltage level of at least one other of the electrical signals to establish a potential for application to the patient to maintain the voltage levels of the received electrical signals within the signal acquisition range.

7. A method as recited in claim 6, further comprising the step of applying the potential to the patient to maintain the voltage levels of the received electrical signals within the signal acquisition range.

8. A heart monitoring system for conducting a heart test on a human patient, the heart monitoring system comprising:
   a plurality of electrodes, the electrodes receiving electrical signals indicative of heart activity of a human patient, the electrical signals having associated voltage levels;
   a plurality of conductors connected to corresponding electrodes;
   a signal acquisition system connected to the conductors and having a signal acquisition range, the signal acquisition system detecting the electrical signals with voltage levels that fall within the signal acquisition range;
   an offset adjustment system operatively coupled to the signal acquisition system, the offset adjustment system using a selected voltage level of at least one of the electrical signals received by an associated electrode to produce an offset adjustment signal;
   a reference signal extracted from at least one of the electrodes; and
   a potential adjusting feedback circuit coupled between the offset adjustment system and a particular one of the electrodes to supply a potential to the particular electrode, the potential adjusting feedback circuit deriving the potential from the offset adjustment signal and a reference signal to maintain the voltage levels of the electrical signals within the signal acquisition range of the signal acquisition system.

9. A heart monitoring system as recited in claim 8, wherein the offset adjustment system comprises:
   a minimum voltage level detector to detect a minimum voltage level from among voltage levels of the electrical signals received by the electrodes; and
   a signal manipulating device to compute the offset adjustment signal as a function of the minimum voltage level.

10. A heart monitoring system as recited in claim 9, wherein the signal manipulating device is coupled to receive both the minimum voltage level and a voltage level of at least one other of the electrical signals, the signal manipulating device computing the offset adjustment signal as a function of both the minimum voltage level and the voltage level of the one other electrical signal.

11. A heart monitoring system as recited in claim 8, wherein the offset adjustment system comprises:

a maximum voltage level detector to detect a maximum voltage level from among voltage levels of the electrical signals received by the electrodes; and a signal manipulating device to compute the offset adjustment signal as a function of the maximum voltage level.

12. A heart monitoring system as recited in claim 11, wherein the signal manipulating device is coupled to receive both the maximum voltage level and a voltage level of at least one other of the electrical signals, the signal manipulating device computing the offset adjustment signal as a function of both the maximum voltage level and the voltage level of the one other electrical signal.

13. A heart monitoring system as recited in claim 8, wherein the signal acquisition system comprises:

a 16-bit analog-to-digital (A/D) converter to convert the electrical signals received by the electrodes to digital values representative of voltage levels of the electrical analog signals.

14. A heart monitoring system as recited in claim 8, wherein the reference signal used by the potential adjusting feedback circuit to derive the potential comprises a voltage level of at least one other of the electrical signals.

15. A heart monitoring system as recited in claim 8, wherein the potential adjusting feedback circuit comprises:

a digital-to-analog (D/A) converter to convert the offset adjustment signal back into an electrical analog signal; and an operational amplifier connected to derive the potential based upon the electrical analog signal output from the D/A converter and at least one of the electrical signals by an electrode.

16. A heart monitoring system for conducting a heart test on a human patient, the heart monitoring system comprising:

a plurality of electrodes, the electrodes receiving electrical analog signals indicative of heart activity of a human patient, the electrical signals having associated voltage levels;

a plurality of conductors connected to corresponding electrodes;

a 16-bit analog-to-digital (A/D) converter operatively coupled to the conductors to convert the electrical analog signals received by the electrodes to digital values representative of the voltage levels associated with the electrical analog signals, the 16-bit A/D converter has a signal acquisition range;

an offset adjustment system operatively coupled to the 16-bit A/D converter, the offset adjustment system using a digital value representative of a voltage level of at least one of the electrical signals to produce an offset adjustment signal;

a reference signal extracted from at least one of the electrodes; and a potential adjusting feedback circuit coupled between the offset adjustment system and a particular one of the electrodes to supply a potential to the particular electrode, the potential adjusting feedback circuit deriving the potential from the offset adjustment signal and a reference signal to maintain the voltage levels of the electrical signals within the signal acquisition range of the 16-bit A/D converter.

17. A heart monitoring system as recited in claim 16, wherein offset adjustment signal is a digital signal and the potential adjusting feedback circuit comprises:

a digital-to-analog (D/A) converter to convert the offset adjustment signal into an electrical analog signal; and an operational amplifier connected to derive the potential using the electrical analog signal output from the D/A converter and at least one electrical analog signal received by an electrode.

* * * * *